(12) United States Patent
Sugimoto et al.

(10) Patent No.: US 11,598,729 B2
(45) Date of Patent: Mar. 7, 2023

(54) X-RAY INSPECTION DEVICE

(71) Applicant: ISHIDA CO., LTD., Kyoto (JP)

(72) Inventors: Kazuyuki Sugimoto, Ritto (JP); Kosuke Fuchuya, Ritto (JP)

(73) Assignee: ISHIDA CO., LTD., Kyoto (JP)

( * ) Notice: Subject to any disclaimer, the term of this patent is extended or adjusted under 35 U.S.C. 154(b) by 766 days.

(21) Appl. No.: 16/491,788

(22) PCT Filed: Mar. 9, 2018

(86) PCT No.: PCT/JP2018/009125
§ 371 (c)(1),
(2) Date: Sep. 6, 2019

(87) PCT Pub. No.: WO2018/168668
PCT Pub. Date: Sep. 20, 2018

(65) Prior Publication Data
US 2020/0041423 A1    Feb. 6, 2020

(30) Foreign Application Priority Data

Mar. 14, 2017  (JP) .............................. JP2017-048198

(51) Int. Cl.
*G01N 23/04* (2018.01)
*G01N 33/02* (2006.01)
*G01N 23/18* (2018.01)

(52) U.S. Cl.
CPC .............. *G01N 23/04* (2013.01); *G01N 23/18* (2013.01); *G01N 33/02* (2013.01);
(Continued)

(58) Field of Classification Search
CPC ........ G01N 23/04; G01N 23/18; G01N 33/02; G01N 2223/03; G01N 2223/302;
(Continued)

(56) References Cited

U.S. PATENT DOCUMENTS

| 2010/0057380 A1 | 3/2010 | Kabumoto |
| 2013/0101172 A1 | 4/2013 | Parikh et al. |

FOREIGN PATENT DOCUMENTS

| EP | 2159570 A2 * | 3/2010 | ........... G01N 23/083 |
| EP | 2159570 A2 | 3/2010 | |

(Continued)

OTHER PUBLICATIONS

The extended European search report dated Feb. 3, 2021.
(Continued)

*Primary Examiner* — Mark R Gaworecki
(74) *Attorney, Agent, or Firm* — Global IP Counselors, LLP

(57) ABSTRACT

An X-ray inspection apparatus suppresses anomalies in inspection results caused by the X-ray inspection apparatus being used while an unsuitable setting is in effect. The X-ray inspection apparatus is provided with an inspection unit, a setting unit, a storage unit, an assessment unit, and a notification unit. The inspection unit inspects an irradiated article using detection data obtained by detecting X-rays. The setting unit sets a setting value used in inspection of the article by the inspection unit. The storage unit stores a detection value based on the detection data. The assessment unit assesses, on the basis of the detection value stored in the storage unit, whether or not the setting value set by the setting unit is suitable. When the assessment unit has assessed that the setting value is not suitable, the notification unit issues a notification to indicate that the setting value is not suitable.

11 Claims, 13 Drawing Sheets

(52) U.S. Cl.
CPC ... *G01N 2223/03* (2013.01); *G01N 2223/302* (2013.01); *G01N 2223/306* (2013.01); *G01N 2223/401* (2013.01); *G01N 2223/50* (2013.01); *G01N 2223/618* (2013.01); *G01N 2223/643* (2013.01); *G01N 2223/645* (2013.01); *G01N 2223/652* (2013.01)

(58) Field of Classification Search
CPC ....... G01N 2223/306; G01N 2223/401; G01N 2223/50; G01N 2223/618; G01N 2223/643; G01N 2223/645; G01N 2223/652
See application file for complete search history.

(56) References Cited

FOREIGN PATENT DOCUMENTS

| JP | H06-309585 A | 11/1994 | |
|---|---|---|---|
| JP | H0933342 A | 2/1997 | |
| JP | 2002-228761 A | 8/2002 | |
| JP | 2007033126 A | 2/2007 | |
| JP | 2007333562 A | 12/2007 | |
| JP | 2010-071790 A | 4/2010 | |
| JP | 2011099725 A | 5/2011 | |
| JP | 2016-075523 A | 5/2016 | |
| JP | 2016200495 A | 12/2016 | |
| WO | 91/19188 A1 | 12/1991 | |
| WO | WO-2006137919 A2 * | 12/2006 | ............. G01N 23/06 |

OTHER PUBLICATIONS

Translation of the Written Opinion of the International Searching Authority, dated Sep. 17, 2019.
The Second Office Action in the corresponding Chinese Patent Application No. 201880017255.5, dated Jan. 25, 2022.
An Information Statement submitted by the Third Party on Mar. 12, 2021.
Translation of the Written Opinion of the International Searching Authority, dated Apr. 17, 2018.

* cited by examiner

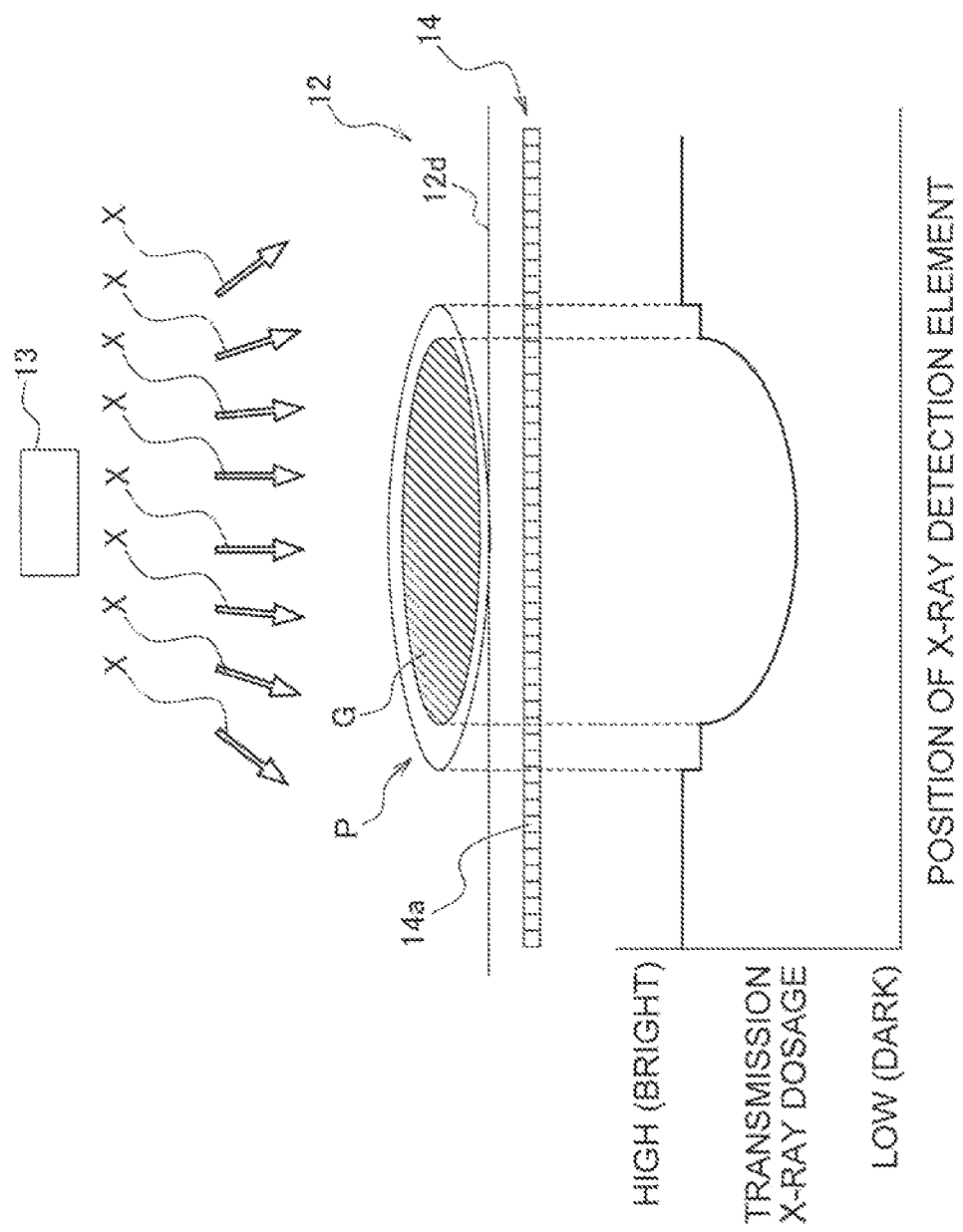
F I G. 5

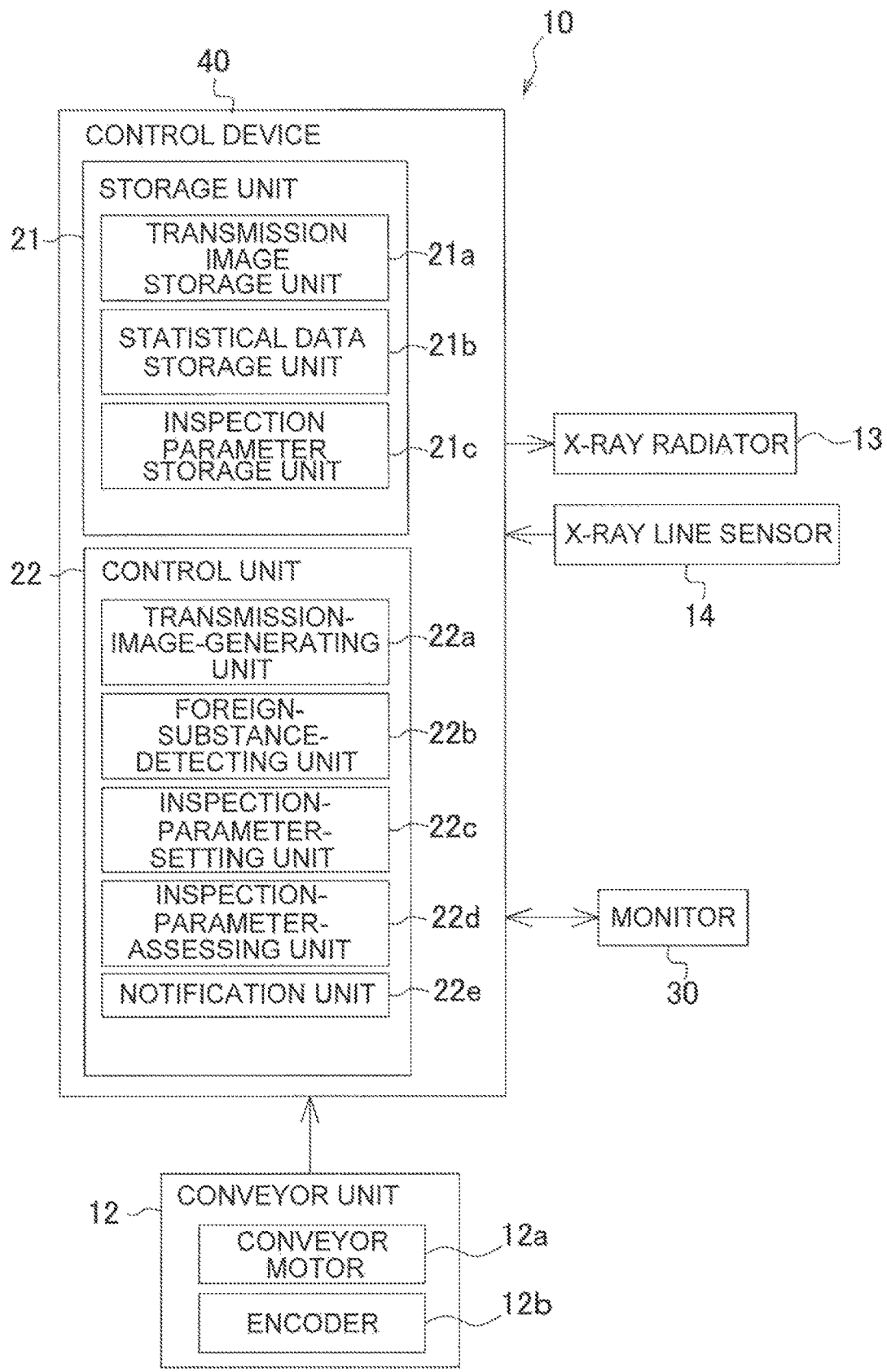
F I G. 6

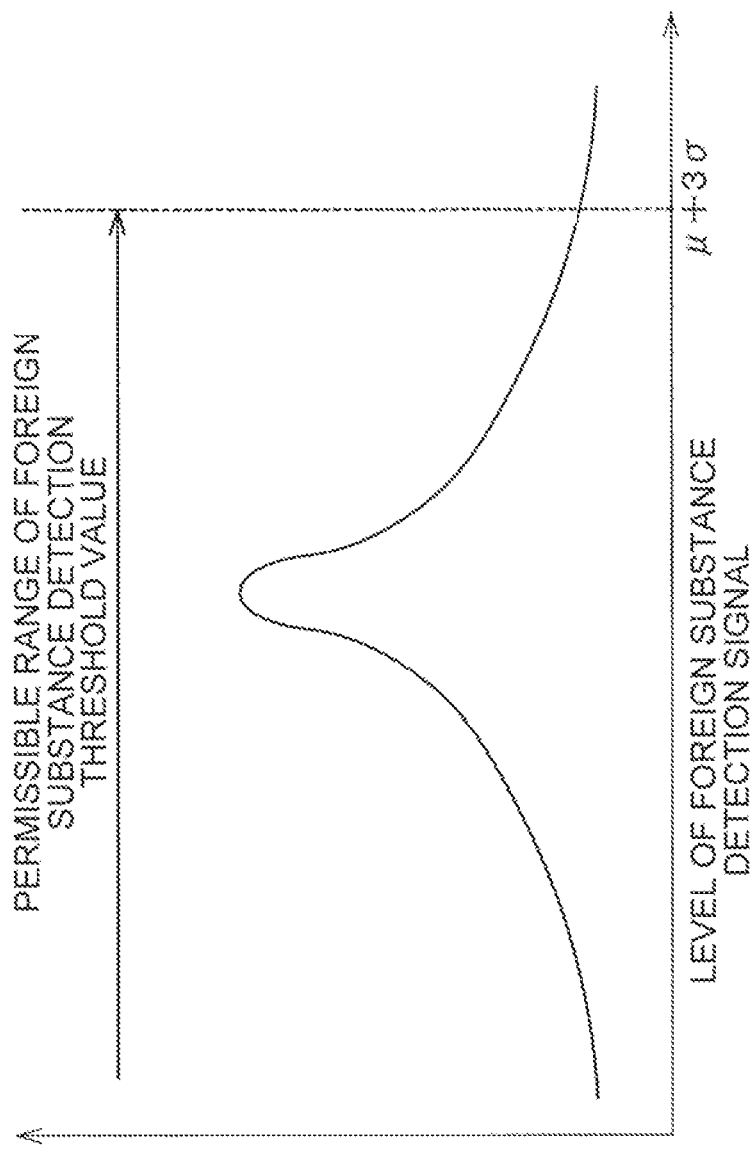
F I G. 9

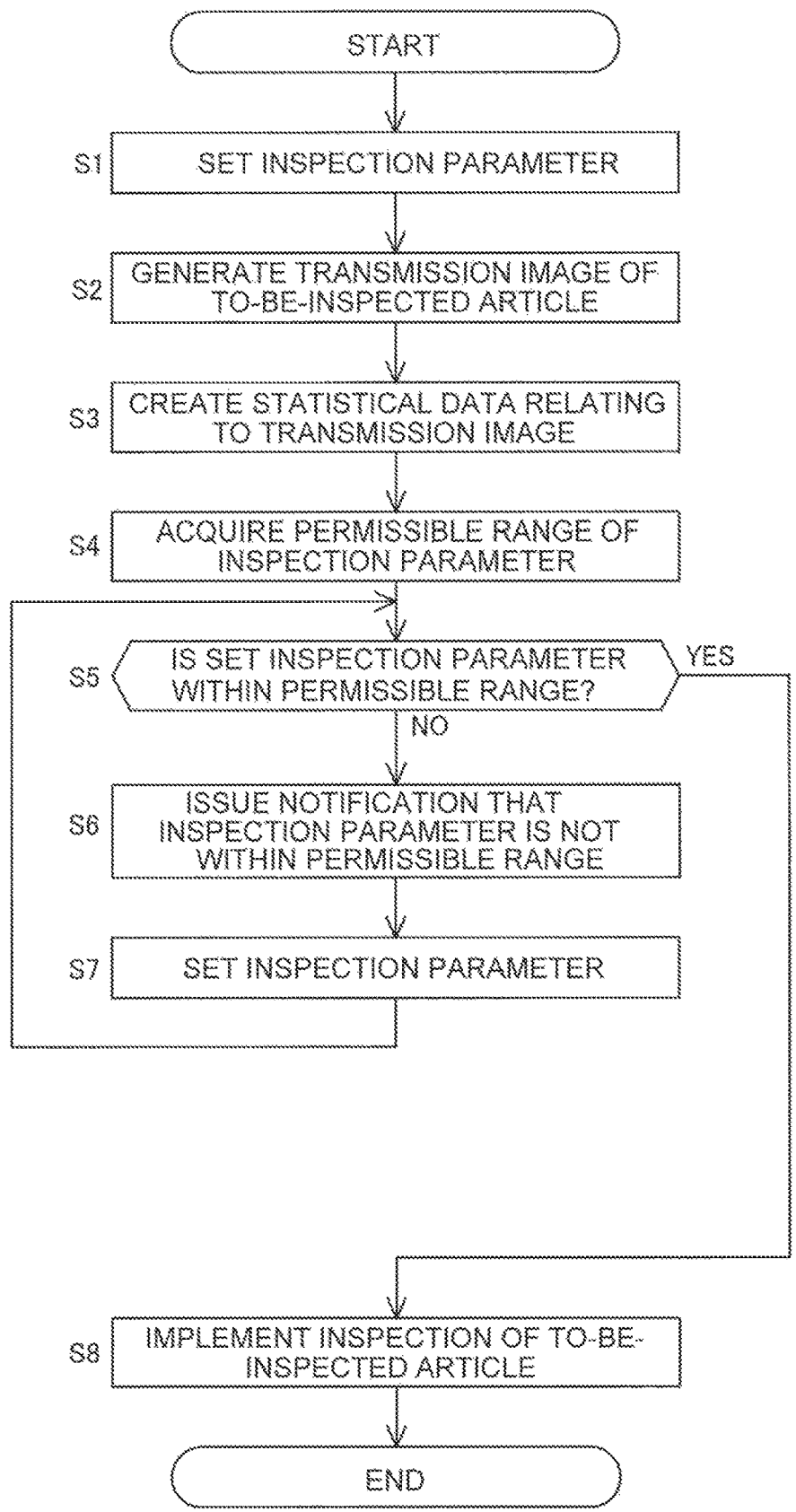
F I G. 10

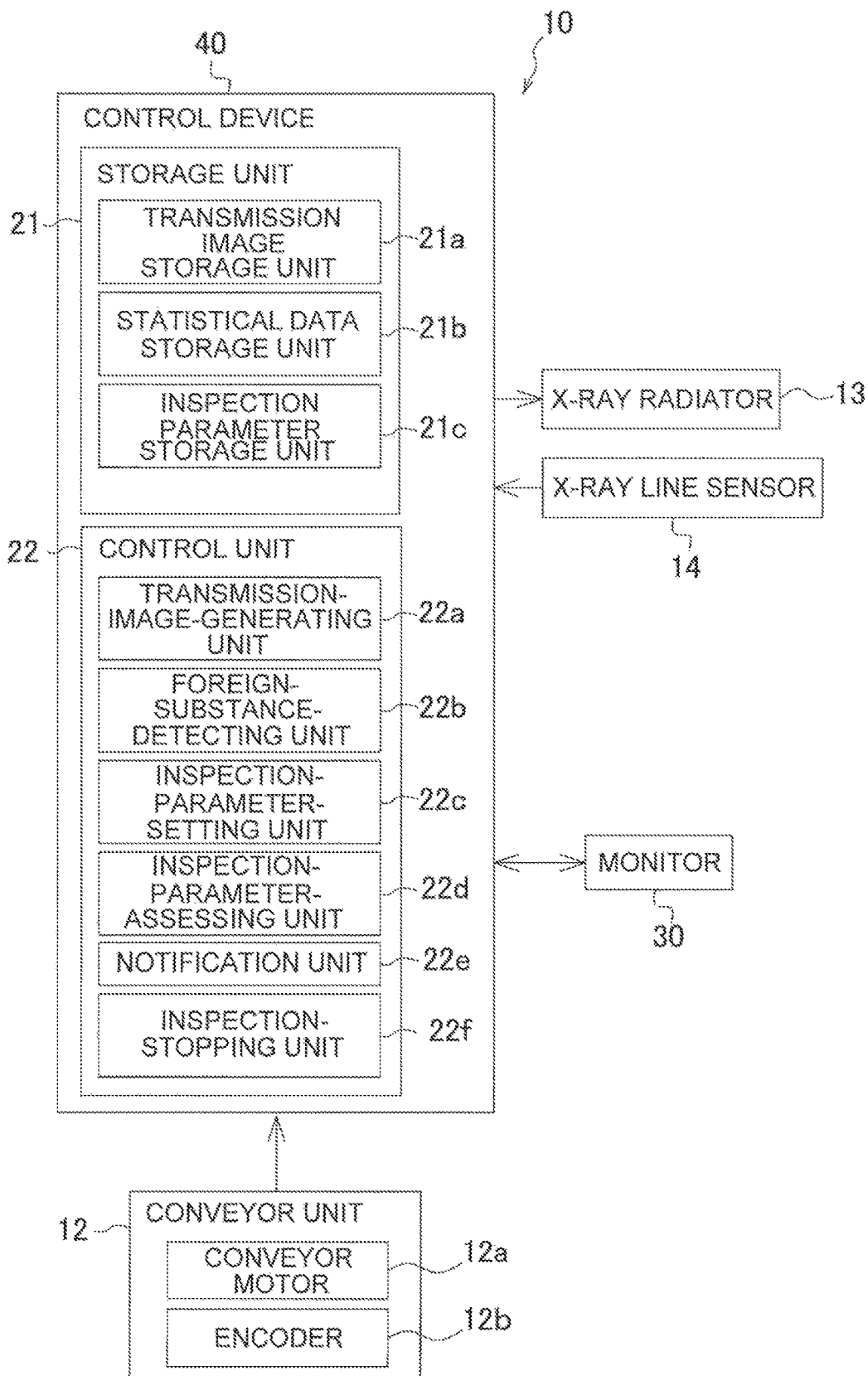
F I G. 11

X-RAY INSPECTION DEVICE

CROSS-REFERENCE TO RELATED APPLICATIONS

This U.S. National stage application of PCT/JP2018/009125 claims priority under 35 U.S.C. § 119(a) to Japanese Patent Application No. 2017-048198, filed in Japan on Mar. 14, 2017, the entire contents of which are hereby incorporated herein by reference.

TECHNICAL FIELD

The present invention relates to an X-ray inspection apparatus configured to irradiate a food product or another such article with X-rays and in order to inspect the article.

BACKGROUND ART

X-ray inspection apparatuses to irradiate a food product or another such article with X-rays and in order to inspect the article have been widely used in the past, as disclosed in Japanese Laid-open Patent Publication No. 2002-228761. Such an X-ray inspection apparatus causes the article to be irradiated with X-rays and inspects the article on the basis of detection data obtained by detecting X-rays transmitted through the article. The X-ray inspection apparatus inspects, e.g., whether there are foreign substances contaminating a food product that is the article.

SUMMARY OF THE INVENTION

Technical Problem

However, in inspection by X-ray inspection apparatuses, anomalies may arise in inspection results if a setting prior to use of the X-ray inspection apparatuses is not correctly configured. A setting relating to a detection signal pertaining to a foreign substance included in a food product that is an article is described as an example. When a level of the detection signal pertaining to the foreign substance exceeds a prescribed threshold value, the level being obtained on the basis of detection data of X-rays transmitted through the article, the X-ray inspection apparatus assesses that the foreign substance has been detected. In this case, if the threshold value for the level of the detection signal pertaining to the foreign substance is set high by a user of the X-ray inspection apparatus, the foreign substance might not be detected even when having contaminated the article. Thus, when a setting of the X-ray inspection apparatus is not suitable, or when a setting pertaining to, inter alia, a maintenance work time of the X-ray inspection apparatus is temporarily changed, an anomaly may arise in the inspection results and performance of the X-ray inspection apparatus will not be adequately exhibited.

An object of the present invention is to provide an X-ray inspection apparatus with which it is possible to suppress the incidence of anomalies in inspection results caused by the X-ray inspection apparatus being used while an unsuitable setting is in effect.

Solution to Problem

An X-ray inspection apparatus according to the present invention is provided with an inspection unit, a setting unit, a storage unit, an assessment unit, and a notification unit. The inspection unit inspects an article using detection data obtained by detecting X-rays with which the article has been irradiated. The setting unit is for setting a setting value used in inspection of the article by the inspection unit. The storage unit stores a detection value based on the detection data. The assessment unit assesses, on the basis of the detection value stored in the storage unit, whether or not the setting value set by the setting unit is suitable. The notification unit issues a notification to indicate that the setting value is not suitable when the assessment unit has assessed that the setting value is not suitable.

The X-ray inspection apparatus according to the present invention acquires a prescribed detection value on the basis of detection data pertaining to, inter alia, an X-ray transmission image of the article. The detection value is, e.g., a level of a detection signal pertaining to a foreign substance included in the article. In this case, a user of the X-ray inspection apparatus sets as a setting value (inspection parameter), e.g., a threshold value for a detection value (foreign substance detection threshold value) serving as a criterion for assessment of the foreign substance included in the article. The X-ray inspection apparatus assesses whether or not the setting value set by the user is suitable on the basis of statistical data pertaining to the detection value, and, when the setting value is not suitable, notifies the user that such an event has occurred. This prevents erroneous setting of the setting value by the user, therefore making it possible for the user to use the X-ray inspection apparatus through causing the X-ray inspection apparatus to exhibit adequate performance. Therefore, the X-ray inspection apparatus can suppress the incidence of anomalies in inspection results caused by the X-ray inspection apparatus being used while an unsuitable setting is in effect.

In the X-ray inspection apparatus according to the present invention, the assessment unit preferably acquires a permissible range of the setting value on the basis of the detection value stored in the storage unit, and assesses that the setting value set by the setting unit is not suitable when the setting value is not within the permissible range.

According to the aspect described above, the X-ray inspection apparatus acquires the permissible range of the setting value on the basis of, inter alia, the statistical data pertaining to the detection value. The X-ray inspection apparatus notifies the user that the setting value set by the user is not suitable when the set setting value is not within the permissible range. Therefore, the X-ray inspection apparatus can suppress the incidence of anomalies in inspection results caused by the X-ray inspection apparatus being used while an unsuitable setting is in effect.

The X-ray inspection apparatus according to the present invention is preferably furthermore provided with a stopping unit. The stopping unit stops inspection of the article by the inspection unit when the assessment unit has assessed that the setting value is not suitable.

According to the aspect described above, when the setting value set by the user is not suitable, the X-ray inspection apparatus notifies the user that such an event has occurred and stops inspection of the article. Therefore, the X-ray inspection apparatus can forcibly terminate unsuitable inspection of the article.

The X-ray inspection apparatus according to the present invention is preferably furthermore provided with a changing unit. The changing unit changes the setting value when the assessment unit has assessed that the setting value is not suitable.

According to the aspect described above, when the setting value set by the user is not suitable, the X-ray inspection apparatus notifies the user that such an event has occurred and changes the setting value. Therefore, the X-ray inspection apparatus can automatically initiate suitable inspection of the article.

In the X-ray inspection apparatus according to the present invention, the inspection unit preferably inspects the article on the basis of a plurality of inspection criteria. In this case, the setting unit is preferably capable of setting a setting value for each of the inspection criteria. In addition, the assessment unit preferably assesses, for each of the inspection criteria, whether or not the setting value set by the setting unit is suitable.

According to the aspect described above, for example, when a foreign substance included in the article is detected, inspection criteria pertaining to each range of dimensions of the to-be-detected foreign substance are set in the X-ray inspection apparatus. The user of the X-ray inspection apparatus can set a setting value for each of the inspection criteria. Therefore, the X-ray inspection apparatus can suppress the incidence of anomalies in inspection results caused by the X-ray inspection apparatus being used while an unsuitable setting is in effect, even when a plurality of types of inspection are performed.

In the X-ray inspection apparatus according to the present invention, the inspection unit preferably senses the foreign substance included in the article.

According to the aspect described above, the X-ray inspection apparatus can suppress the incidence of an anomaly in which it is assessed that no foreign substance is included in the article in a case where the foreign substance is included in the article.

Advantageous Effects of Invention

The X-ray inspection apparatus according to the present invention can suppress the incidence of anomalies in inspection results caused by the X-ray inspection apparatus being used while an unsuitable setting is in effect.

BRIEF DESCRIPTION OF THE DRAWINGS

FIG. 5 is a graph showing an example of a transmission X-ray dosage (detection amount) detected by X-ray detection elements 14a of an X-ray line sensor 14;

FIG. 6 is a block diagram of a control device 40;

FIG. 9 is one example of statistical data pertaining to a level of a foreign substance detection signal stored in a statistical data storage unit 21b;

FIG. 10 is a flow chart of a process to assess whether or not a foreign substance detection threshold value used in inspecting contamination by a foreign substance is suitable;

FIG. 11 is a block diagram of a control device 40 in modification A;

DESCRIPTION OF EMBODIMENTS

An embodiment of the present invention is described with reference to the accompanying drawings. The embodiment described below is one specific example of the present invention and in no way limits the technical scope thereof.

(1) Overall Configuration of X-Ray Inspection Apparatus

Figure 1:
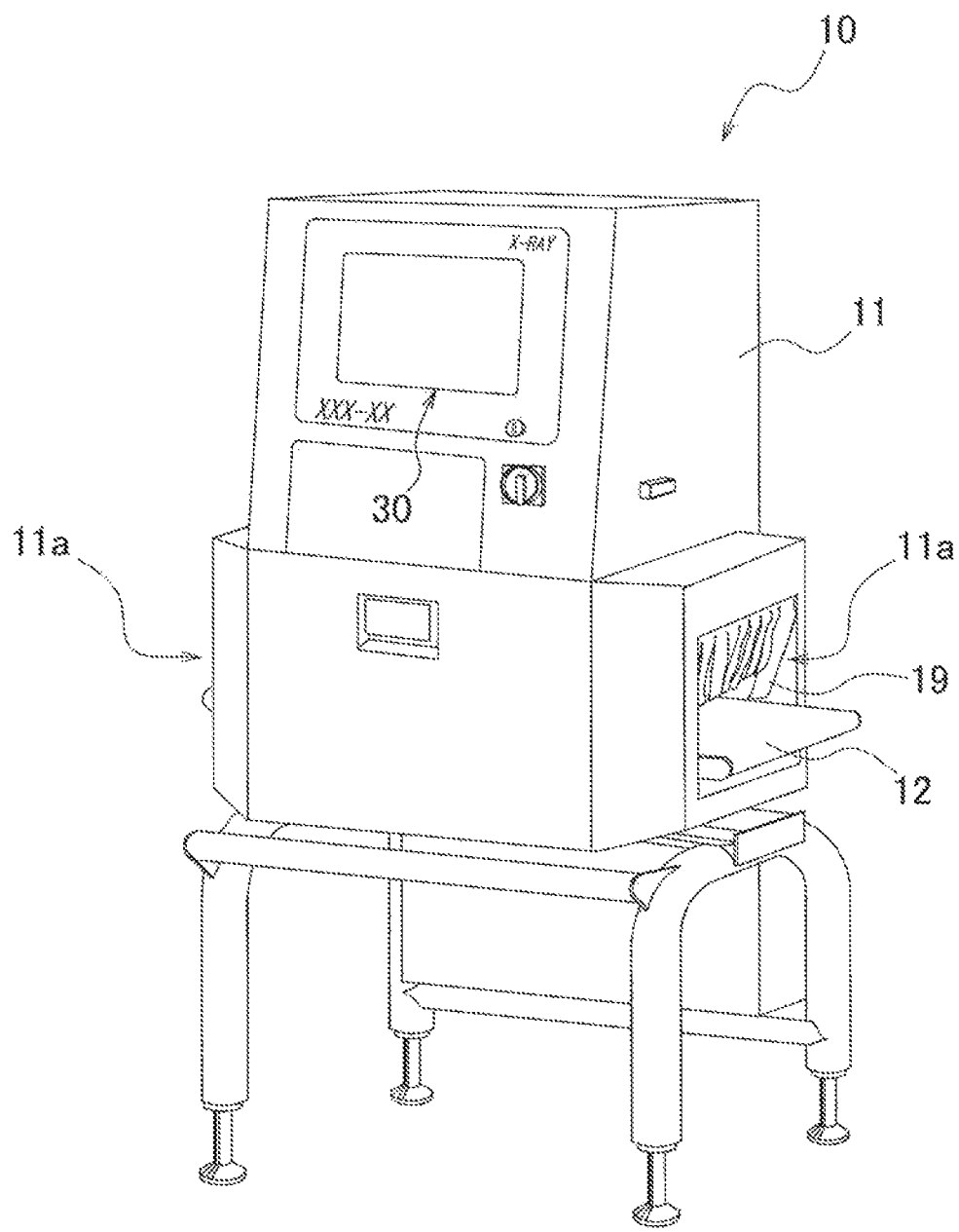
FIG. 1 is a perspective view showing an external appearance of an X-ray inspection apparatus 10 that is one embodiment of the present invention.
Figure 2:
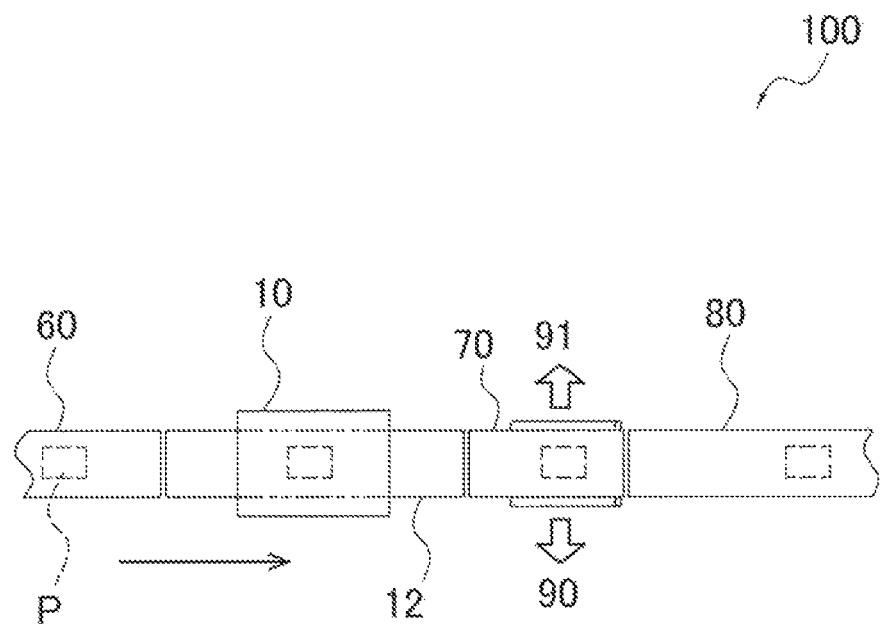
FIG. 2 is a schematic illustration of an inspection line 100 in which the X-ray inspection apparatus 10 is incorporated.

FIG. 1 is a perspective view showing an external appearance of an X-ray inspection apparatus 10 that is one embodiment of the present invention. FIG. 2 is a schematic illustration of an inspection line 100 in which the X-ray inspection apparatus 10 is incorporated. The inspection line 100 inspects an article P. In the inspection line 100, the article P is conveyed to the X-ray inspection apparatus 10 by a preceding conveyor 60. The conveyance direction of the article P is indicated by an arrow in FIG. 2.

The X-ray inspection apparatus 10 causes the article P, which is continuously conveyed by the preceding conveyor 60, to be irradiated with X-rays to determine quality of the article P. Specifically, the X-ray inspection apparatus 10 inspects contamination of the article P by a foreign substance and classifies the article P as a superior or inferior product on the basis of an inspection result. The inspection of contamination by a foreign substance involves detecting a foreign substance contaminating the article P. In a case where the article P is a food product, the foreign substance is, e.g., a fragment of iron, stainless steel, or another such metal. The X-ray inspection apparatus 10 inspects contamination by the foreign substance, classifying an article P in which there is no contamination by the foreign substance as a superior product, and classifying a article P in which there is contamination by the foreign substance as an inferior product.

The result of the inspection performed by the X-ray inspection apparatus 10 is sent to a sorting mechanism 70 disposed downstream from the X-ray inspection apparatus 10. The sorting mechanism 70 sends products P determined to be superior products by the X-ray inspection apparatus 10 to a line conveyor unit 80 to discharge the superior products. The sorting mechanism 70 sorts products P determined to be inferior products by the X-ray inspection apparatus 10 in inferior-product-discharge directions 90, 91 and discharges said products P from the inspection line 100.

Figure 3:
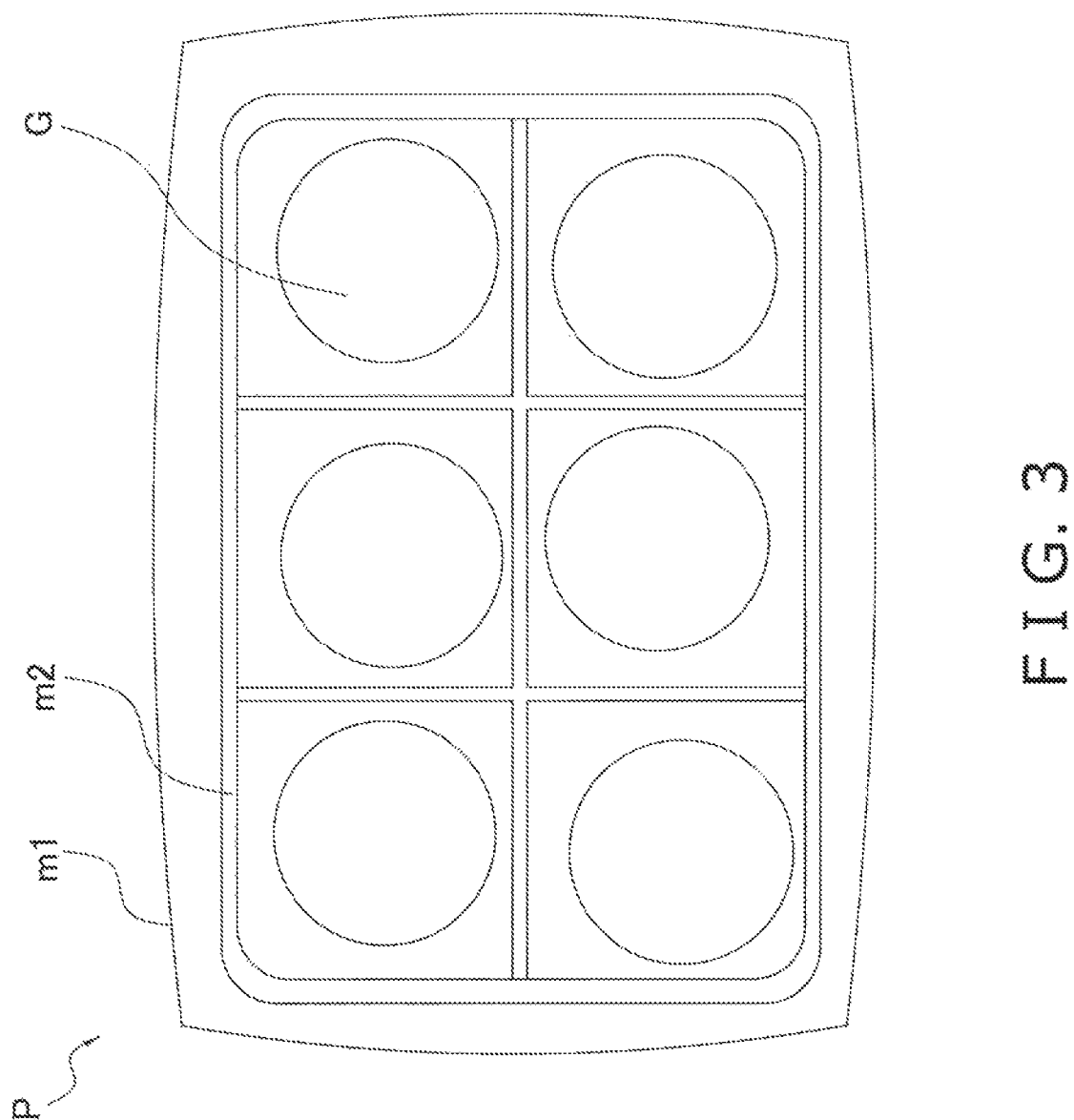
FIG. 3 is a schematic plan view of an article P.

In the present embodiment, the article P that is subject to inspection by the X-ray inspection apparatus 10 is a packaged food product. FIG. 3 is a schematic plan view of the article P. The article P is composed of a plurality of contents G, a packaging material m1, and a partition material m2. The contents G are food products having a prescribed shape. The contents G are, e.g., cylindrical baked sweets. The packaging material m1 is a bag-form plastic film for packaging the contents G and the partition material m2. The partition material m2 is a plastic tray for partitioning a plurality of contents G in prescribed numbers thereof, the partition material m2 being positioned inside the packaging material m1. The plurality of contents G are lined up inside the packaging material m1 so as not to overlap each other.

(2) Detailed Configuration of X-Ray Inspection Apparatus

The X-ray inspection apparatus 10 is mainly configured from a shield box 11, a conveyor unit 12, an X-ray radiator 13, an X-ray line sensor 14, a monitor 30, and a control device 40.

(2-1) Shield Box

Figure 4:
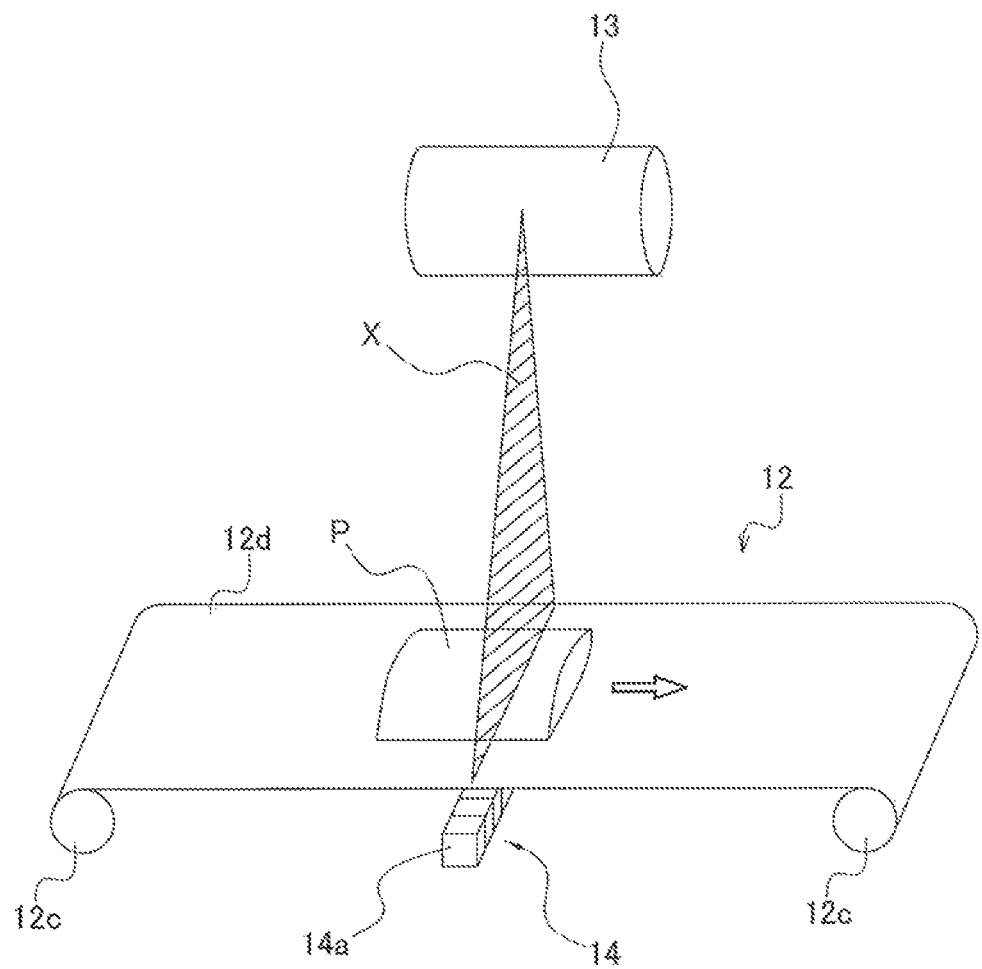
FIG. 4 is a schematic illustration of an interior of a shield box 11 of the X-ray inspection apparatus 10.

FIG. 4 is a schematic illustration of an interior of the shield box 11 of the X-ray inspection apparatus 10. The shield box 11 is a casing of the X-ray inspection apparatus 10. The shield box 11 has openings 11a for conveying the article P in and out, the openings 11a being formed in two side surfaces, as shown in FIG. 1. The openings 11a are used in order to convey the article P from outside the shield box 11 into the interior thereof, and in order to convey the article P from the interior of the shield box 11 to the outside. The openings 11a are covered by shielding curtains 19. The shielding curtains 19 suppress leakage of X-rays from the interior of the shield box 11 to the outside. The shielding curtains 19 are molded from a lead-containing rubber. The shielding curtains 19 are pushed aside by the article P when the article P is conveyed in and out.

The interior of the shield box 11 accommodates the conveyor unit 12, the X-ray radiator 13, the X-ray line sensor 14, the control device 40, etc. (see FIG. 6). The monitor 30, an insertion slot for a key, a power switch, etc., are disposed in an upper part of a front surface of the shield box 11.

(2-2) Conveyor Unit

The conveyor unit 12 is a belt conveyor for conveying the article P inside the shield box 11. The conveyor unit 12 is disposed so as to pass through the openings 11a formed in the two side surfaces of the shield box 11, as shown in FIG. 1.

The conveyor unit 12 mainly has conveyor rollers 12c and an endless belt 12d, as shown in FIG. 4. The conveyor rollers 12c are driven by a conveyor motor 12a. The belt 12d rotates due to driving of the conveyor rollers 12c, and the article P on the belt 12d is conveyed. A conveyance direction of the article P is shown by an arrow in FIG. 4.

A conveyance speed of the article P conveyed by the conveyor unit 12 changes in accordance with a setting speed inputted by an operator who is a user of the X-ray inspection apparatus 10. The control device 40 performs an inverter control of the conveyor motor 12a on the basis of the setting speed and controls the conveyance speed of the article P. An encoder 12b for detecting the conveyance speed achieved by the conveyor unit 12 and transmitting said speed to the control device 40 is mounted on the conveyor motor 12a (see FIG. 6).

(2-3) X-Ray Radiator

The X-ray radiator 13 is disposed above the conveyor unit 12, as shown in FIG. 4. The X-ray radiator 13 radiates a fan-shaped beam of X-rays (radiant light) toward the X-ray line sensor 14 disposed below the article P. As shown in FIG. 4, an X-ray radiation region X is perpendicular to a conveyance surface of the conveyor unit 12 and extends in a direction orthogonal to the conveyance direction of the article P conveyed by the conveyor unit 12. Specifically, the X-rays radiated from the X-ray radiator 13 expand along a width direction of the belt 12d.

(2-4) X-Ray Line Sensor

The X-ray line sensor 14 is a sensor to sense transmission X-rays, which are X-rays that have been transmitted through the article P and the conveyor unit 12. The X-ray line sensor 14 is disposed below the conveyor unit 12, as shown in FIG. 4. The X-ray line sensor 14 is mainly configured from a plurality of X-ray detection elements 14a. The X-ray detection elements 14a are disposed horizontally in a linear manner along a direction orthogonal to the conveyance direction of the article P conveyed by the conveyor unit 12.

The X-ray line sensor 14 detects the transmission X-rays and outputs X-ray transmission signals to indicate a voltage that corresponds to an intensity of the detected transmission X-rays. The brightness (lightness/shading) of an X-ray image (transmission image) is determined according to the X-ray transmission signals. FIG. 5 is a graph showing an example of a transmission X-ray dosage (detection amount) detected by the X-ray detection elements 14a of the X-ray line sensor 14. A horizontal axis of the graph corresponds to positions of the X-ray detection elements 14a. The horizontal axis of the graph corresponds to a position in a horizontal direction (width direction of the belt 12d) orthogonal to the conveyance direction of the conveyor unit 12. A vertical axis of the graph shows the transmission X-ray dosage (detection amount) detected by the X-ray detection elements 14a. In the transmission image, locations having a high detection amount are displayed in a bright (light) manner, and locations having a low detection amount are displayed in a dark (shaded) manner. Specifically, the brightness/darkness (lightness/shading) of the transmission image corresponds to the detection amount of the transmission X-rays. As shown in FIG. 5, the detection amount of X-rays transmitted through the contents G is lower than the detection amount of X-rays not transmitted through the contents G.

The X-ray line sensor 14 also functions as a sensor for sensing a timing at which the article P passes through the fan-shaped X-ray radiation region X (see FIG. 4). Specifically, the X-ray line sensor 14 outputs X-ray transmission signals (first signals) to indicate a voltage equal to or less than a prescribed threshold value when the article P being conveyed on the belt 12d of the conveyor unit 12 has reached a position above the X-ray line sensor 14 (a position overlapping the radiation region X). The X-ray line sensor 14 outputs X-ray transmission signals (second signals) to indicate a voltage exceeding the prescribed threshold value when the article P has passed out of the radiation region X. The first signals and the second signals are transmitted to the control device 40, whereby the presence/absence of the article P in the radiation region X is detected.

(2-5) Monitor

The monitor 30 is a liquid-crystal display provided with a touch-panel function. The monitor 30 functions as a display unit and an input unit of the X-ray inspection apparatus 10. The monitor 30 displays, inter alia, the inspection result pertaining to the article P. The monitor also displays, inter alia, a screen image for inputting an initial setting of the X-ray inspection apparatus 10 and a parameter relating to the determination of the quality of the article P.

The operator of the X-ray inspection apparatus 10 can manipulate the monitor 30 and input, inter alia, an inspection parameter and operation setting information. The inspection parameter is a parameter used in order to assess the quality of the article P. Specifically, the inspection parameter is, inter alia, a threshold value of transmission X-ray dosage used in order to discern the contents G included in the article P and a foreign substance contaminating the article P. The operation setting information is information pertaining to, inter alia, the inspection speed of the article P and the conveyance direction of the conveyor unit 12.

The monitor 30 is connected to the control device 40 and transmits/receives signals to/from the control device 40. The inspection parameter and the operation setting information inputted by the monitor 30 are stored in a storage unit 21 of the control device 40.

(2-6) Control Device

The control device 40 is a computer configured mainly from a CPU, a ROM, a RAM, a hard disk (HDD), etc. The control device 40 is provided with a display control circuit, a key input circuit, a communication port, etc. (not shown). The display control circuit is a circuit to control a display of data by the monitor 30. The key input circuit is a circuit to take in key input data inputted by the operator via a touch panel of the monitor 30. The communication port is a port to enable connection with printers and other such devices, as well as with LANs and other such networks.

FIG. 6 is a block diagram of the control device 40. The control device 40 mainly has the storage unit 21 and a control unit 22. The control device 40 is electrically connected to the conveyor unit 12, the X-ray radiator 13, the X-ray line sensor 14, and the monitor 30. The control device 40 is electrically connected to the conveyor motor 12a and the encoder 12b of the conveyor unit 12. The control device 40 acquires data relating to the speed of the conveyor motor 12a from the encoder 12b and calculates a movement distance of the article P on the basis of the data. The control device 40 receives the X-ray transmission signals outputted from the X-ray line sensor 14 and detects a timing at which the article P on the belt 12d of the conveyor unit 12 reaches the X-ray radiation region X.

The control device 40 discerns the presence/absence of a foreign substance contaminating the article P on the basis of the transmission X-ray dosage (detection amount) and assesses the quality of the article P. The control device 40 assesses that a article P in which no foreign substance was detected is a superior product, and that a article P in which the foreign substance was detected is an inferior product. An inferior product is, e.g., a article P in which a metal fragment or another such foreign substance is packaged in the packaging material nil together with the contents G.

(2-6-1) Storage Unit

The storage unit 21 stores the inspection parameter, the operation setting information, and various programs executed by the control unit 22. The inspection parameter and the operation setting information are inputted by the operator using the touch-panel function of the monitor 30.

The storage unit 21 mainly has a transmission image storage unit 21a, a statistical data storage unit 21b, and an inspection parameter storage unit 21c.

(a) Transmission Image Storage Unit

The transmission image storage unit 21a stores detection data that is data relating to the transmission image generated by a transmission-image-generating unit 22a (described below). The transmission image is an X-ray image based on the transmission X-ray dosage detected by the X-ray line sensor 14.

Figure 7:
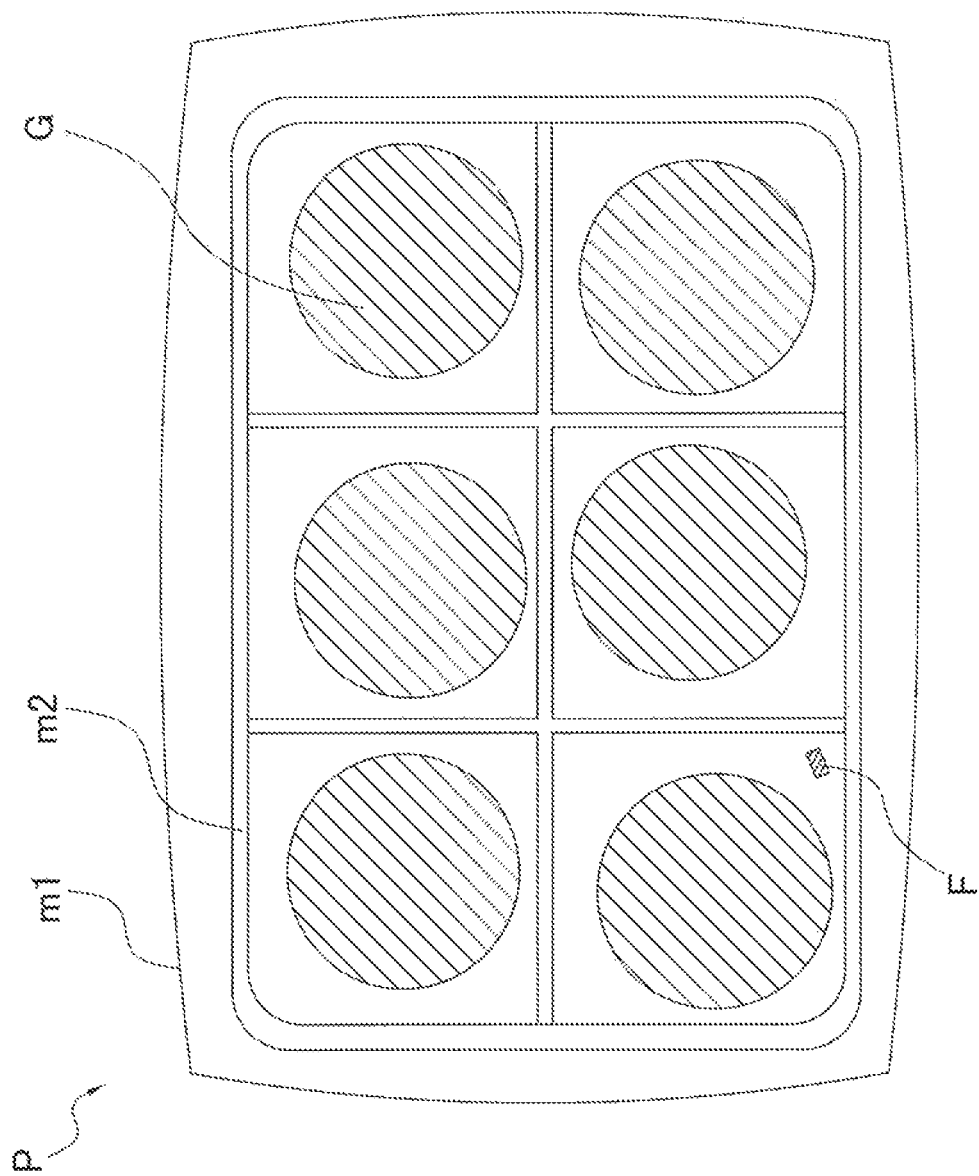
FIG. 7 is an illustration of an example of a transmission image of the article P.

FIG. 7 is an illustration of an example of the transmission image of the article P. In FIG. 7, a foreign substance F that is a metal fragment has contaminated the article P. The transmission image shown in FIG. 7 is configured from a plurality of pixels. Each of the pixels in the transmission image has one of a plurality of concentration levels. The concentration levels of the pixels in the transmission image correspond to the detection amount of X-rays. Specifically, the detection amount of X-rays at each pixel is lower commensurately with a higher concentration level of the pixel. In FIG. 7, the concentration level of the transmission image is represented by spacing between hatch marks. Specifically, the concentration levels of pixels constituting a given region are higher commensurately with a smaller spacing between the hatch marks in the given region.

As shown in FIG. 7, the transmission image of the article P includes pixels that correspond to each of the contents G included in the article P, the foreign substance F, the packaging material m1, and the partition material m2. The contents G are thicker than the packaging material m1 and the partition material m2, and X-rays are not as readily transmitted through the contents G. Therefore, under normal circumstances, the detection amount of X-rays transmitted through the contents G is less than the detection amount of X-rays transmitted through the packaging material m1 and the partition material m2. X-rays are transmitted even less readily through the metal foreign substance F than through the contents G, which are food products. Therefore, under normal circumstances, the detection amount of X-rays transmitted through the foreign substance F is less than the detection amount of X-rays transmitted through the contents G.

In the transmission image of the article P shown in FIG. 7, the pixels that correspond to the contents G are displayed so as to be darker (more shaded) than the pixels that correspond to the packaging material m1 and the partition material m2, and the pixels that correspond to the foreign substance F are displayed so as to be darker (more shaded) than the pixels that correspond to the contents G.

(b) Statistical Data Storage Unit

The statistical data storage unit 21b records data relating to a level of a foreign substance detection signal, which is acquired by a foreign-substance-detecting unit 22b (described below) by analyzing the transmission image of the article P, and stores said data as statistical data pertaining to the level of the foreign substance detection signal. The level of the foreign substance detection signal, as well as further details pertaining to the statistical data and a method to use the statistical data, are described below.

(c) Inspection Parameter Storage Unit

The inspection parameter storage unit 21c stores the inspection parameter set by the operator using an inspection-parameter-setting unit 22c (described below). Further details pertaining to the inspection parameter and a method to use the inspection parameter are described below.

(2-6-2) Control Unit

By executing various programs stored in the storage unit 21, the control unit 22 has functions of the transmission-image-generating unit 22a, the foreign-substance-detecting unit 22b, the inspection-parameter-setting unit 22c, an inspection-parameter-assessing unit 22d, and a notification unit 22e.

(a) Transmission-Image-Generating Unit

The transmission-image-generating unit 22a generates the X-ray image (transmission image) on the basis of the transmission X-ray dosage detected by the X-ray line sensor 14. Specifically, the transmission-image-generating unit 22a acquires X-ray transmission signals outputted from the X-ray detection elements 14a of the X-ray line sensor 14 over a short time interval, and generates the transmission image on the basis of the acquired X-ray transmission signals. Specifically, the transmission-image-generating unit 22a generates the transmission image of the article P (see FIG. 7) on the basis of the X-ray transmission signals outputted from the X-ray detection elements 14a when the article P passes through the fan-shaped X-ray radiation region X (see FIG. 4). The presence/absence of the article P in the radiation region X is determined according to a signal outputted by the X-ray line sensor 14, The transmission-image-generating unit 22a joins together data for each time interval chronologically as a matrix, the data relating to the intensity (luminance) of the transmission X-rays obtained from the X-ray detection elements 14a, and generates the transmission image of the article P. The transmission image generated by the transmission-image-generating unit 22a is stored in the transmission image storage unit 21a as detection data.

(b) Foreign-Substance-Detecting Unit

The foreign-substance-detecting unit 22b detects the foreign substance F contaminating the article P using the transmission image of the article P and inspects the article P. The transmission image used by the foreign-substance-detecting unit 22b is the detection data generated by the transmission-image-generating unit 22a and stored in the transmission image storage unit 21a.

The foreign-substance-detecting unit 22b analyzes the transmission image using an image-processing algorithm, and detects a region corresponding to the foreign substance F included in the transmission image when the foreign substance F has contaminated the article P. The image-processing algorithm processes the transmission image so that it is easy to differentiate between a region that corresponds to the foreign substance F and a region that corresponds to the contents G, the packaging material m1, and the partition material m2 in the transmission image. The image-processing algorithm processes the transmission image on the basis of, e.g., an area of a low-transmission region that is a region in which the intensity of transmission X-rays is low, a change in the intensity of the transmission X-rays between the low-transmission region and a surrounding region, etc. There is a strong possibility that the low-transmission region is a region that corresponds to the metal foreign substance F, which does not readily transmit X-rays.

The foreign-substance-detecting unit 22b is capable of detecting the foreign substance F using a plurality of image-processing algorithms in accordance with characteristics of the to-be-detected foreign substance F. The plurality of image-processing algorithms are, e.g., an algorithm suited to detecting a miniscule foreign substance F less than 1 mm in size, an algorithm suited to detecting a needle-shaped foreign substance F, and an algorithm suited to detecting a foreign substance F having a large area. The foreign-substance-detecting unit 22b detects the foreign substance F using each of the plurality of image-processing algorithms in accordance with a shape and an area of the to-be-detected foreign substance F. This makes it possible for the foreign-substance-detecting unit 22b to analyze the transmission image of the article P and detect foreign substances F that have a variety of shapes and areas and contaminate the article P.

Figure 8:
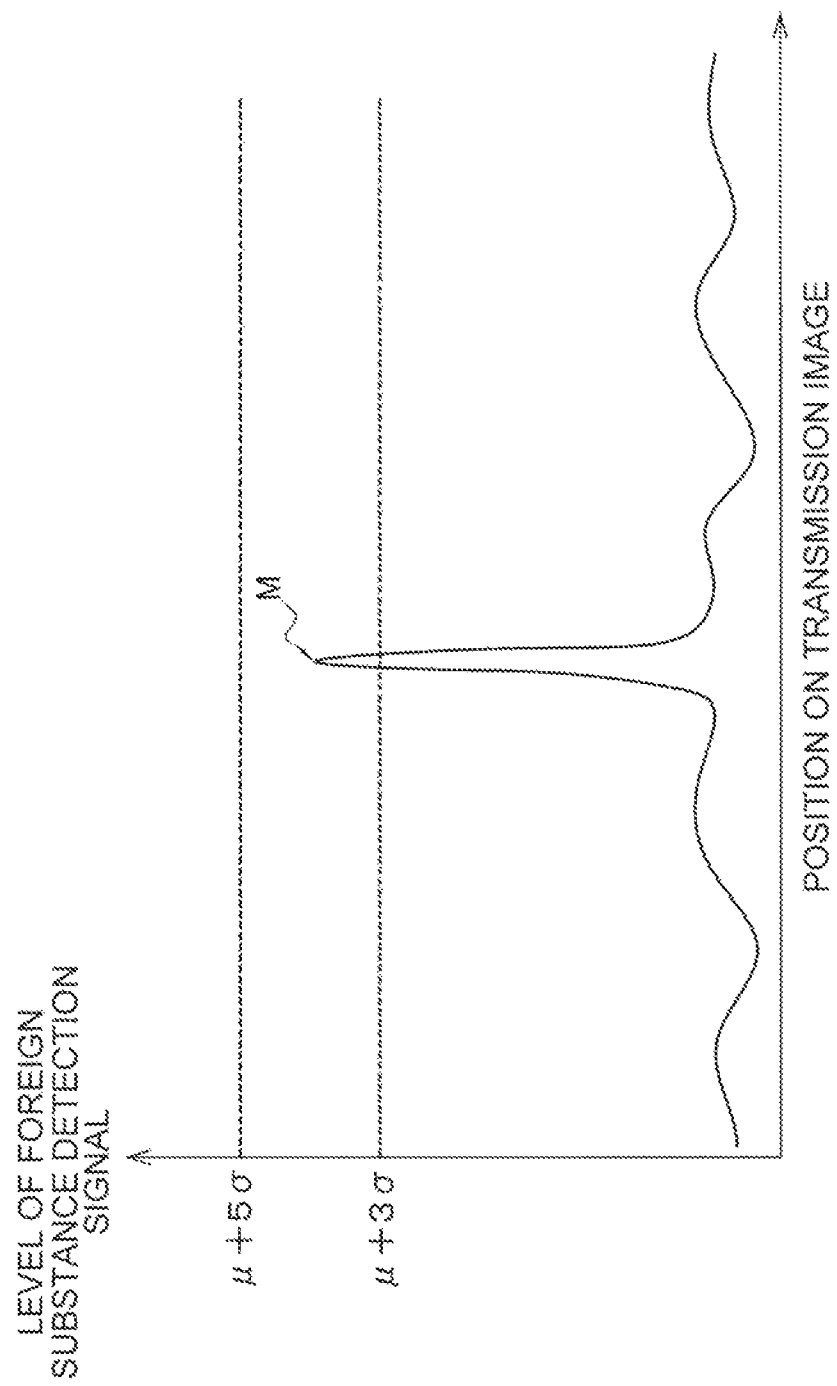
FIG. 8 is one example of a graph representing a result of analysis of the transmission image of the article P by a foreign-substance-detecting unit 22b, which performs the analysis using an image-processing algorithm.

FIG. 8 is one example of a graph representing a result of analysis of the transmission image of the article P by the foreign-substance-detecting unit 22b, which performs the analysis using the image-processing algorithm. FIG. 8 corresponds to data representing the transmission image processed by the image-processing algorithm. A horizontal axis of the gram represents a position on the transmission image, in FIG. 8, for expediency, the position on the transmission image, which is two-dimensional data, is represented as one-dimensional data running along the horizontal axis of the graph. A vertical axis of the graph shows the level of the foreign substance detection signal (for the foreign substance F) included in the article P. The level of the foreign substance detection signal is acquired from results of analysis of the transmission image according to the image-processing algorithm. As shown in FIG. 8, when a peak in the level of the foreign substance detection signal is present in the graph, there is a strong possibility that the foreign substance F is present near a position of the peak. The peak in the level of the foreign substance detection signal is a portion where a value of the level projects higher than in surrounding portions. Conversely, when no peak in the level of the foreign substance detection signal is present in the graph, there is a possibility that no foreign substance F is included in the article P.

The foreign-substance-detecting unit 22b assesses whether or not a foreign substance has contaminated the article P on the basis of the value of the peak in the level of the foreign substance detection signal. Specifically, when a maximum value M of the peak in the level of the foreign substance detection signal in FIG. 8 exceeds a prescribed threshold value represented by a dotted line in FIG. 8, the foreign-substance-detecting unit 22b assesses that the foreign substance F has contaminated the article P. Through this method, the foreign-substance-detecting unit 22b is capable of analyzing the transmission image of the article P and detecting the foreign substance F included in the article P.

Data that relates to the level of the foreign substance detection signal and is acquired by the foreign-substance-detecting unit 22b by analyzing the transmission image is recorded in the statistical data storage unit 21b. The data relating to the level of the foreign substance detection signal is recorded in the statistical data storage unit 21b each time the foreign-substance-detecting unit 22b analyzes the transmission image of the article P. At such time, the statistical data storage unit 21b stores the data relating to the level of the foreign substance detection signal as statistical data.

FIG. 9 is one example of statistical data pertaining to the level of the foreign substance detection signal stored in the statistical data storage unit 21b. FIG. 9 shows a normal distribution curve representing the statistical data. The normal distribution curve is a distribution curve of the level of the foreign substance detection signal acquired by analyzing numerous transmission images. The term "numerous transmission images" refers to, e.g., 100 or more transmission images. A horizontal axis of a graph represents the level of the foreign substance detection signal. A vertical axis of the graph represents a frequency of appearance of a corresponding level of the foreign substance detection signal in the statistical data.

(c) Inspection-Parameter-Setting Unit

The inspection-parameter-setting unit 22c is a program for setting an inspection parameter used in order to discern the contents G included in the article P and the foreign substance F contaminating the article P. The operator can input a variety of inspection parameters by, e.g., using the touch-panel function of the monitor 30.

Hereinbelow, the inspection parameter is a foreign substance detection threshold value. The foreign substance detection threshold value is a threshold value pertaining to the level of the foreign substance detection signal. The foreign-substance-detecting unit 22b assesses that the foreign substance F has contaminated the article P when the maximum value M of the peak in the level of the foreign substance detection signal exceeds the foreign substance detection threshold value (see FIG. 8).

(d) Inspection-Parameter-Assessing Unit

The inspection-parameter-assessing unit 22d assesses whether or not the inspection parameter set by the operator using the inspection-parameter-setting unit 22c is suitable. In cases where the inspection parameter is the foreign substance detection threshold value (threshold value pertaining to the level of the foreign substance detection signal), the inspection-parameter-assessing unit 22d assesses whether or not the foreign substance detection threshold value set by the operator is within a prescribed permissible range. The inspection-parameter-assessing unit 22d assesses that the set foreign substance detection threshold value is suitable when the foreign substance detection threshold value is within the permissible range, and assesses that the set foreign substance detection threshold value is not suitable when the foreign substance detection threshold value is not within the permissible range.

The inspection-parameter-assessing unit 22d is configured to use a range of $\mu+3\sigma$ as the permissible range of the foreign substance detection threshold value when the statistical data pertaining to the level of the foreign substance detection signal is represented by a normal distribution curve. $\mu$ represents the average of the normal distribution curve, and $\sigma$ represents the standard deviation of the normal distribution curve. The inspection-parameter-assessing unit 22d calculates $\mu$ and $\sigma$ on the basis of the statistical data pertaining to the level of the foreign substance detection signal as stored in the statistical data storage unit 21b. FIG. 9 shows a range of $\mu+3\sigma$ or less as the permissible range of the foreign substance detection threshold value. In this case, when the foreign substance detection threshold value set by the operator using the inspection-parameter-setting unit 22c is greater than an upper-limit value $\mu+3\sigma$ of the permissible range, the inspection-parameter-assessing unit 22d assesses that the set foreign substance detection threshold value is not within the permissible range and therefore is not suitable.

A description is given here as to whether or not the foreign-substance-detecting unit 22b is capable of detecting the foreign substance F on the basis of the data shown in FIG. 8 in a case where the foreign substance F has contaminated the article P and the foreign substance detection threshold value set by the operator is $\mu+5\sigma$. The operator does not set the foreign substance detection threshold value directly to "$\mu+5\sigma$," but rather sets said value to a numeric value. The graph shown in FIG. 8 shows a peak in the level of the foreign substance detection signal. FIG. 8 shows the threshold value $\mu+3\sigma$ and the threshold value $\mu+5\sigma$ as horizontal dotted lines. In FIG. 8, the maximum value M of the peak in the level of the foreign substance detection signal is lower than the threshold value $\mu+5\sigma$ set by the operator. Therefore, because the maximum value M of the peak in the level of the foreign substance detection signal does not exceed the threshold value $\mu+5\sigma$, the foreign-substance-detecting unit 22b erroneously assesses that the foreign substance F has not contaminated the article P. However, when the foreign substance detection threshold value set by the operator is $\mu+3\sigma$ under the same conditions, the maximum value M of the peak in the level of the foreign substance detection signal is higher than the threshold value $\mu+3\sigma$ set by the operator in FIG. 8. Therefore, because the maximum value M of the peak in the level of the foreign substance detection signal exceeds the threshold value $\mu+3\sigma$, the foreign-substance-detecting unit 22b correctly assesses that the foreign substance F has contaminated the article P.

Thus, the foreign-substance-detecting unit 22b might be incapable of correctly assessing whether or not the foreign substance F has contaminated the article P in accordance with the foreign substance detection threshold value set by the operator. The inspection-parameter-assessing unit 22d acquires the permissible range of the foreign substance detection threshold value on the basis of the statistical data pertaining to the level of the foreign substance detection signal, assesses that the foreign substance detection threshold value set by the operator is suitable when the foreign substance detection threshold value is within the permissible range, and assesses that the foreign substance detection threshold value set by the operator is not suitable when the foreign substance detection threshold value is not within the permissible range.

Typically when the foreign substance detection threshold value is set high, erroneous detection in which the foreign substance F is assessed to have been detected even when no foreign substance F has contaminated the article P does not often occur. However, there is a concern that the foreign substance F will not be detected even when having contaminated the article P. Conversely, when the foreign substance detection threshold value is set low, detection sensitivity pertaining to the foreign substance F is improved in cases where the foreign substance F has contaminated the article P. However, erroneous detection in which the foreign substance F is assessed to have been detected even when no foreign substance F has contaminated the article P might occur more often. Therefore, it is necessary for the foreign substance detection threshold value to be suitably set in accordance with, inter alia, characteristics of the article P and the foreign substance F. The inspection-parameter-assessing unit 22d is capable of acquiring the permissible range, which is a suitable range for the foreign substance detection threshold value, on the basis of the statistical data pertaining to the level of the foreign substance detection signal. Therefore, the inspection-parameter-assessing unit 22d has a function to suppress erroneous detection of the foreign substance F.

(e) Notification Unit

When the inspection-parameter-assessing unit 22d has assessed that the foreign substance detection threshold value, which is the inspection parameter set by the operator, is not suitable, the notification unit 22e notifies the operator that such an event has occurred. Specifically, the notification unit 22e displays on the liquid-crystal display of the monitor 30 an indication that the foreign substance detection threshold value, which is the inspection parameter set using the inspection-parameter-setting unit 22c, is not within the permissible range acquired by the inspection-parameter-assessing unit 22d. For example, the liquid-crystal display of the monitor 30 displays a message such as "Threshold value for level of foreign substance detection signal is not suitable," "Please reduce threshold value for level of foreign substance detection signal," or "Foreign substance could go undetected."

(3) Operation of X-Ray Inspection Apparatus

Next, a description is given as to a process in which the control device 40 of the X-ray inspection apparatus 10 assesses suitability of the foreign substance detection threshold value used in inspecting contamination by the foreign substance to detect the foreign substance F included in the article P on the basis of the transmission image of the article P. FIG. 10 is a flow chart of a process to assess whether or not the foreign substance detection threshold value used in inspecting contamination by the foreign substance is suitable.

In step S1, the inspection parameter is set before initiation of the inspection of contamination by the foreign substance by the X-ray inspection apparatus 10. The inspection parameter is used in order to discern the foreign substance F contaminating the article P. The inspection parameter is the foreign substance detection threshold value (threshold value pertaining to the level of the foreign substance detection signal) acquired from analysis results pertaining to the transmission image generated in a subsequent step S2. In this case, the foreign substance detection threshold value us used by the foreign-substance-detecting unit 22b as the inspection parameter in order to assess whether or not the foreign substance F has contaminated the article P. A default value of the foreign substance detection threshold value is set in advance before the initiation of the inspection of contamination by the foreign substance, or the foreign substance detection threshold value is set by the operator of the X-ray inspection apparatus 10 using the inspection-parameter-setting unit 22c.

In step S2, the transmission image of the article P is generated. Specifically, the transmission-image-generating unit 22a generates transmission images in a quantity that is suitable for creating the statistical data in a subsequent step S3.

In step S3, the statistical data relating to the suitable quantity of transmission images generated in step S2 is created. Specifically, the statistical data storage unit 21b records data relating to the level of the foreign substance detection signal obtained by the foreign-substance-detecting unit 22b analyzing the transmission images, and stores said data as statistical data pertaining to the level of the foreign substance detection signal (see FIG. 9).

In step S4, the permissible range of the inspection parameter is acquired on the basis of the statistical data created in step S3. Specifically, the inspection-parameter-assessing unit 22d acquires the permissible range of the foreign substance detection threshold value on the basis of the statistical data pertaining to the level of the foreign substance detection signal.

In step S5, it is assessed whether or not the inspection parameter set in step S1 is within the permissible range of the inspection parameter acquired in step S4. Specifically, the inspection-parameter-assessing unit 22d assesses whether or not the set foreign substance detection threshold value is within the permissible range. The process proceeds to step S6 when the foreign substance detection threshold value is not within the permissible range, but proceeds to step S8 when the foreign substance detection threshold value is within the permissible range.

In step S6, a notification is issued to indicate that the inspection parameter is not within the permissible range. Specifically, the notification unit 22e displays on the liquid-crystal display of the monitor 30 an indication that the foreign substance detection threshold value, which is the inspection parameter set in step S1, is not suitable.

In step S7, the inspection parameter is set. Specifically, when the operator of the X-ray inspection apparatus 10 is notified in step S6 that the foreign substance detection threshold value is not suitable, the operator resets the foreign substance detection threshold value using the inspection-parameter-setting unit 22c. It is re-assessed in step S5 whether or not the foreign substance detection threshold value reset in step S7 is within the permissible range.

In step S8, inspection of article P is implemented. Specifically, the foreign substance detection threshold value set in step S1 is used by the foreign-substance-detecting unit 22b to inspect contamination by the foreign substance into the article P. The transmission image of the article P is generated according to the inspection of contamination by the foreign substance into the article P. Therefore, in the inspection of contamination by the foreign substance into the article P, it is permissible to transition to step S3 as necessary and recreate the statistical data on the basis of the generated transmission image. A more suitable permissible range of the inspection parameter is acquired in step S4 due to recreation of the statistical data.

(4) Features

The X-ray inspection apparatus 10 performs an inspection of contamination by the foreign substance to detect the foreign substance F included in the article P on the basis of the transmission image of the article P. In the inspection of contamination by the foreign substance, the X-ray inspection apparatus 10 assesses that the foreign substance F has contaminated the article P when the maximum value M of the peak in the level of the foreign substance detection signal obtained from the transmission image of the article is greater than the foreign substance detection threshold value (see FIG. 8). The X-ray inspection apparatus 10 has a function, in cases where the setting of the foreign substance detection threshold value used in the inspection of contamination by the foreign substance is not suitable, to issue a notification that such an event has occurred, as described below. The operator of the X-ray inspection apparatus 10 can reset the foreign substance detection threshold value designated as not being suitable.

Specifically, the X-ray inspection apparatus 10 creates the statistical data pertaining to the level of the foreign substance detection signal on the basis of the data relating to the level of the foreign substance detection signal as acquired by analyzing a plurality of transmission images of the article P (see FIG. 9). The X-ray inspection apparatus 10 acquires the permissible range of the foreign substance detection threshold value on the basis of the statistical data pertaining to the level of the foreign substance detection signal. The X-ray inspection apparatus 10 assesses whether or not the foreign substance detection threshold value used in inspecting contamination by the foreign substance into the article P is within the permissible range. The X-ray inspection apparatus 10 notifies the operator that the setting of the foreign substance detection threshold value is not suitable when the foreign substance detection threshold value is not within the permissible range.

This prevents unsuitable setting and erroneous setting of the foreign substance detection threshold value by the operator of the X-ray inspection apparatus 10, therefore making it possible for the operator to use the X-ray inspection apparatus 10 through causing the X-ray inspection apparatus 10 to exhibit adequate performance. For example, the X-ray inspection apparatus 10 is capable of suppressing erroneous detection in which the foreign substance F is assessed to not be included in the article P even when having contaminated the article P. Therefore, the X-ray inspection apparatus 10 is capable of suppressing the incidence of anomalies in inspection results caused by the X-ray inspection apparatus 10 being used while an unsuitable setting is in effect.

(5) Modifications

One embodiment of the present invention is described above. However, the present invention is not limited to the above embodiment; various changes are possible within a scope that does not depart from the gist of the invention.

(5-1) Modification A

FIG. 11 is a block diagram of a control device 40 in the present modification. As shown in FIG. 11, the control unit 22 of the control device 40 may furthermore have a function of an inspection-stopping unit 22f by executing various programs stored in the storage unit 21. The inspection-stopping unit 22f stops inspection of contamination by the foreign substance into the article P by the foreign-substance-detecting unit 22b when the inspection-parameter-assessing unit 22d has assessed that the inspection parameter set by the operator is not suitable.

In this case, when the setting value set by the operator is not suitable, the X-ray inspection apparatus 10 is capable of notifying the operator that such an event has occurred and forcibly stopping inspection of the article P. Therefore, the X-ray inspection apparatus 10 in the present modification forcibly terminates the inspection when there is a possibility that an unsuitable inspection of the article P is being carried out, thereby making it possible to suppress the incidence of anomalies in inspection results caused by the X-ray inspection apparatus 10 being used while an unsuitable setting is in effect.

In the present modification, the inspection-stopping unit 22f may forcibly stop the inspection of the article P in lieu of the operator of the X-ray inspection apparatus 10 resetting the inspection parameter using the inspection-parameter-setting unit 22c in step S7 shown in FIG. 10 according to the embodiment.

(5-2) Modification B

In the embodiment, the inspection-parameter-assessing unit 22d acquires one permissible range of the foreign substance detection threshold value on the basis of the statistical data pertaining to the level of the foreign substance detection signal. However, the inspection-parameter-assessing unit 22d may acquire a plurality of permissible ranges of the foreign substance detection threshold value on the basis of the statistical data pertaining to the level of the foreign substance detection signal. Next, there is described a process in which, in the X-ray inspection apparatus 10 of modification A, the inspection-parameter-assessing unit 22d: acquires two permissible ranges, i.e., a first permissible range and a second permissible range; and assesses whether or not the set inspection parameter is suitable on the basis of the two permissible ranges. The second permissible range is different from the first permissible range.

Figure 12:
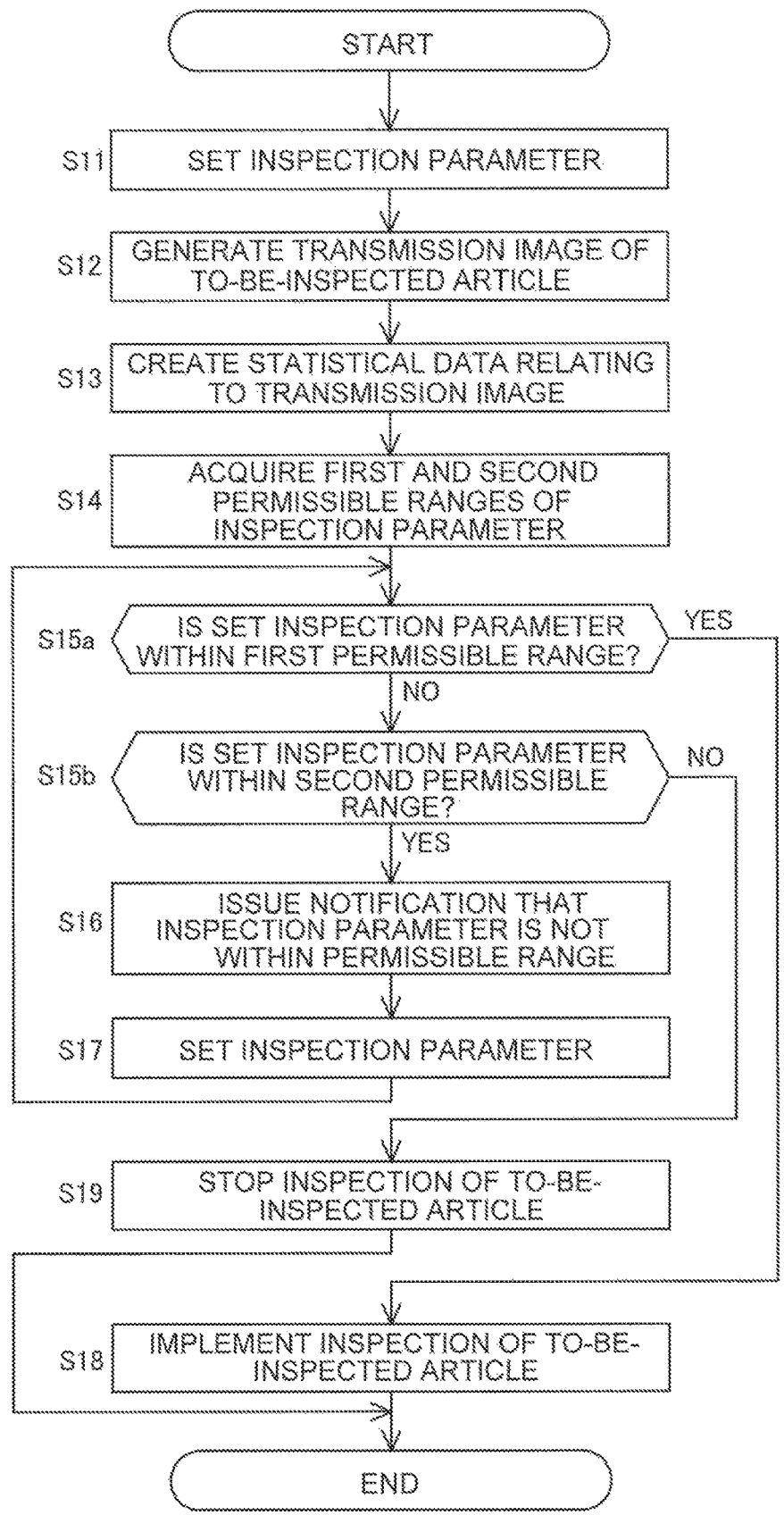
FIG. 12 is a flow chart in which, in modification B, a first permissible range and a second permissible range are used by an inspection-parameter-assessing unit 22d to assess whether or not a set inspection parameter is suitable.

FIG. 12 is a flow chart in which the first permissible range and the second permissible range are used by the inspection-parameter-assessing unit 22d to assess whether or not the inspection parameter set by the operator is suitable.

FIG. 12 shows steps S11 to S18. Steps S11 to S13 are respectively the same processes as steps S1 to S3 in the embodiment shown in FIG. 10.

In step S14, two permissible ranges of the inspection parameter are acquired. Specifically, the inspection-parameter-assessing unit 22d acquires the first permissible range and the second permissible range of the inspection parameter (foreign substance detection threshold value) on the basis of the statistical data pertaining to the level of the foreign substance detection signal, as described above. The first permissible range is a range of $\mu+3\sigma$ or less, and the second permissible range is a range of a range of $\mu+4\sigma$ or less, the second permissible range being broader than the first permissible range.

In step S15a, it is assessed whether or not the inspection parameter set in step S11 is within the first permissible range of the inspection parameter as acquired in step S14. The process proceeds to step S15b when the inspection parameter is not within the first permissible range, but proceeds to step S18 when the inspection parameter is within the first permissible range.

In step S15b, it is assessed whether or not the inspection parameter set in step S11 is within the second permissible range of the inspection parameter as acquired in step S14. The process proceeds to step S19 when the inspection parameter is not within the second permissible range, but proceeds to step S16 when the inspection parameter is within the second permissible range.

In step S16, a notification is issued to indicate that the inspection parameter is not within the permissible range, in the same manner as in step S6 in the embodiment. Specifically, the notification unit 22e displays on the liquid-crystal display of the monitor 30 an indication that the foreign substance detection threshold value, which is the inspection parameter set in step S11, is not suitable.

In step S17, the inspection parameter is set in the same manner as in step S7 in the embodiment. Specifically, when the operator of the X-ray inspection apparatus 10 is notified in step S16 that the foreign substance detection threshold value is not suitable, the operator resets the foreign substance detection threshold value using the inspection-parameter-setting unit 22c. It is re-assessed in step S15a whether or not the foreign substance detection threshold value reset in step S17 is within the first permissible range.

In step S18, the inspection of the article P is implemented. Specifically, the foreign-substance-detecting unit 22b inspects contamination by the foreign substance into the article P using the foreign substance detection threshold value set in step S11. In the inspection of contamination by the foreign substance into the article P, a transmission image of the article is generated. Therefore, in the inspection of contamination by the foreign substance into the article P, it is permissible to transition to step S13 as necessary and recreate the statistical data on the basis of the generated transmission image, in the same manner as in the embodiment.

In step S19, the inspection of the article P is stopped. Specifically, the inspection-stopping unit 22f forcibly stops the inspection of contamination by the foreign substance into the article P by the foreign-substance-detecting unit 22b. After the inspection of contamination by the foreign substance has been stopped, the operator of the X-ray inspection apparatus 10 may reset the foreign substance detection threshold value using the inspection-parameter-setting unit 22c.

A plurality of permissible ranges of the foreign substance detection threshold value are used in the inspection-parameter-assessing unit 22d in the present modification, thereby making it possible to perform different processes according to the inspection parameter when the inspection parameter is not suitable. For example, in the process shown in FIG. 12, it is assessed that the inspection parameter is suitable and the inspection of contamination by the foreign substance into the article P is implemented when the foreign substance detection threshold value, which is the inspection parameter, is equal to or less than $\mu+3\sigma$ (step S18). In addition, it is assessed that the inspection parameter is not suitable and a notification is issued to indicate that the inspection parameter is not within the permissible range when the inspection parameter is greater than $\mu+3\sigma$ and equal to or less than $\mu+4\sigma$ (step S16). Moreover, when the inspection parameter is greater than $\mu+4\sigma$ (step S19), it is assessed that the inspection parameter is not suitable and the inspection of contamination by the foreign substance into the article P is forcibly stopped. Therefore, a plurality of permissible ranges of the inspection parameter are used in the X-ray inspection apparatus 10 in the present modification, thereby making it possible to employ a suitable response that corresponds to the setting value of the inspection parameter.

(5-3) Modification C

Figure 13:
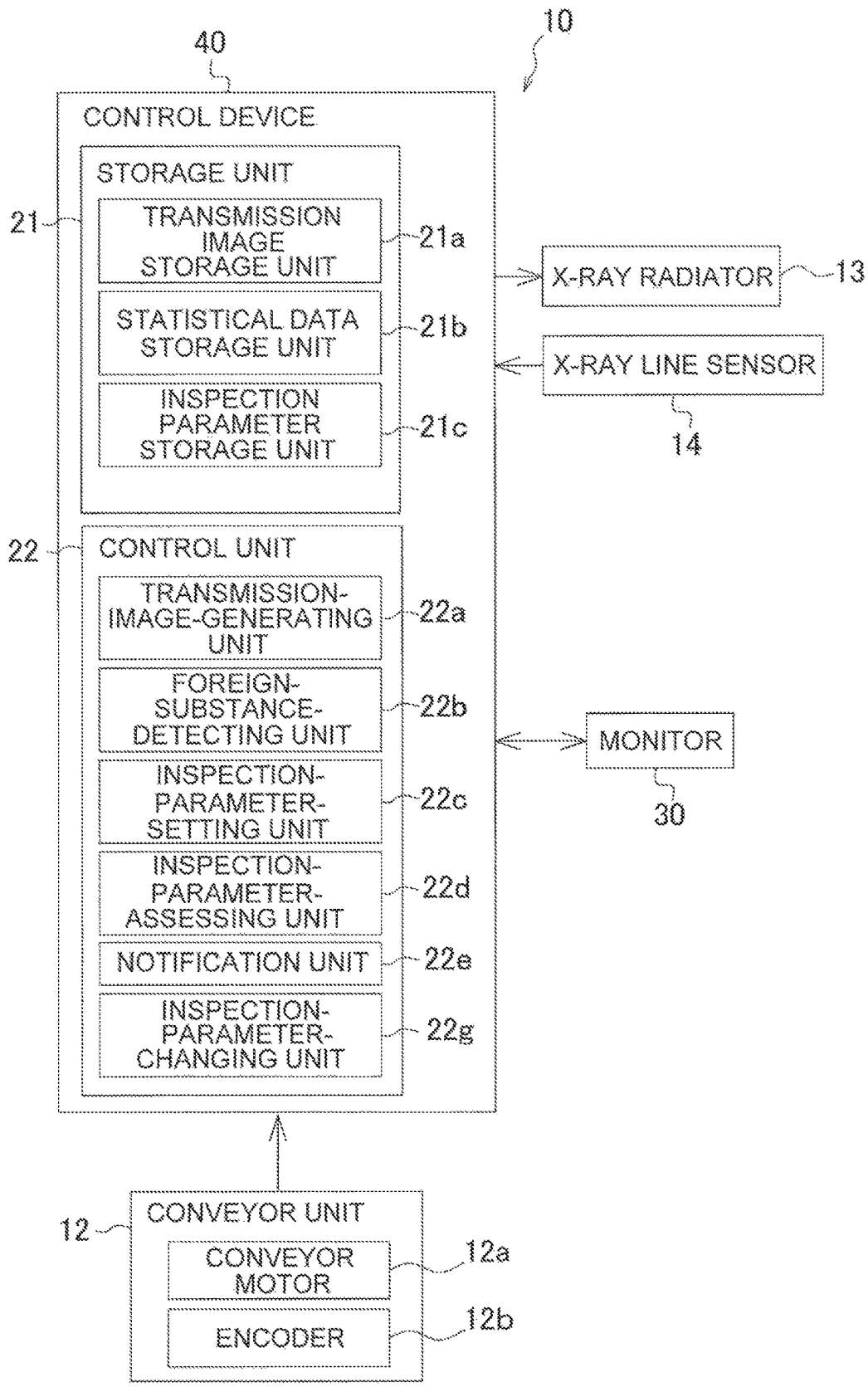
FIG. 13 is a block diagram of a control device 40 in modification C.

FIG. 13 is a block diagram of a control device 40 in the present modification. As shown in FIG. 13, the control unit 22 of the control device 40 may furthermore have a function of an inspection-parameter-changing unit 22g by executing various programs stored in the storage unit 21. The inspection-parameter-changing unit 22g automatically changes the setting value of the inspection parameter when the inspection-parameter-assessing unit 22d has assessed that the inspection parameter set by the operator is not suitable In this case, when the inspection parameter set by the operator is not suitable, the X-ray inspection apparatus 10 is capable of notifying the operator that such an event has occurred and automatically changing the inspection parameter. Therefore, the X-ray inspection apparatus 10 is capable of automatically implementing inspection of the article P in a state in which a suitable inspection parameter has been set.

In the present modification, the inspection-parameter-changing unit 22g may automatically change the inspection parameter in accordance with a prescribed criterion. For example, when it has been assessed that the inspection parameter set by the operator is not suitable, the inspection-parameter-changing unit 22g may raise or lower the inspection parameter by a prescribed value to thereby change the inspection parameter. In this case, the inspection-parameter-assessing unit 22d may re-assess whether or not the inspection parameter changed by the inspection-parameter-changing unit 22g is suitable.

In the present modification, the inspection-parameter-changing unit 22g may automatically change the inspection parameter so as to be within the permissible range of the inspection parameter as acquired by the inspection-parameter-assessing unit 22d.

In the present modification, the inspection-parameter-changing unit 22g may automatically change the inspection parameter in lieu of the operator of the X-ray inspection apparatus 10 resetting the inspection parameter using the inspection-parameter-setting unit 22c in step S7 shown in FIG. 10 according to the embodiment or in step S17 shown in FIG. 12 according to modification B.

(5-4) Modification D

In the X-ray inspection apparatus 10 the foreign-substance-detecting unit 22b is capable of inspecting the article P on the basis of a plurality of inspection criteria. In this case it is preferable that the operator of the X-ray inspection apparatus 10 can set an inspection parameter for each of the inspection criteria using the inspection-parameter-setting unit 22c. In addition, the inspection-parameter-assessing unit 22d preferably assesses, for each of the inspection criteria, whether or not the inspection parameter set by the operator is suitable.

The inspection criteria are procedures to inspect the article P, e.g., image-processing algorithms used in order for the foreign-substance-detecting unit 22b to analyze the transmission image. In this case, it is preferable that the operator can use the inspection-parameter-setting unit 22c to set the inspection parameter for each of the image-processing algorithms used by the foreign-substance-detecting unit 22b.

In the X-ray inspection apparatus 10 in the present modification, the foreign-substance-detecting unit 22b detects the to-be-detected foreign substance F using each of the plurality of image-processing algorithms in accordance with the shape and area of the foreign substance F. In this case, the operator can set the inspection parameter for the image-processing algorithms suited to the shape and area of the to-be-detected foreign substance F in order to detect the foreign substance F included in the article P. This makes it possible for the X-ray inspection apparatus 10 to acquire an optimal permissible range of the inspection parameter in accordance with the characteristics of the to-be-detected foreign substance F, therefore making it possible to detect foreign substances F having a variety of shapes and areas with high accuracy. Therefore, the X-ray inspection apparatus 10 in the present modification can suppress the incidence of anomalies in inspection results caused by the X-ray inspection apparatus 10 being used while an unsuitable setting is in effect, even when a variety of inspections of contamination by the foreign substance are implemented in accordance with the shape and area of the foreign substance F.

What is claimed is:

1. An X-ray inspection apparatus comprising:
   an inspection unit configured to inspect an article using detection data obtained by detecting X-rays with which the article has been irradiated;
   a setting unit for setting a setting value used in inspection of the article by the inspection unit;
   a storage unit to store a detection value based on the detection data;
   an assessment unit to determine, on the basis of the detection value stored in the storage unit, whether or not the setting value set by the setting unit is suitable for inspection of the article, where suitable corresponds to the setting value being within a permissible range and not suitable corresponds to the setting value being not being within the permissible range; and
   a notification unit to issue a notification to indicate that the setting value is not suitable for inspection of the article when the assessment unit has determined that the setting value is not suitable for inspection of the article,
   the assessment unit acquires the permissible range of the setting value on the basis of the detection value stored in the storage unit.

2. The X-ray inspection apparatus according to claim 1, wherein
   the X-ray inspection apparatus furthermore includes a stopping unit to stop inspection of the article by the inspection unit when the assessment unit has determined that the setting value is not suitable for inspection of the article.

3. The X-ray inspection apparatus according to claim 2, wherein
   the X-ray inspection apparatus furthermore includes a changing unit to change the setting value when the assessment unit has determined that the setting value is not suitable for inspection of the article.

4. The X-ray inspection apparatus according to claim 2, wherein:
   the inspection unit inspects the article on the basis of a plurality of inspection criteria;
   the setting unit is capable of setting a setting value for each of the inspection criteria; and
   the assessment unit determines, for each of the inspection criteria, whether or not the setting value set by the setting unit is suitable for inspection of the article.

5. The X-ray inspection apparatus according to claim 2, wherein
   the inspection unit is configured to detect foreign substances included in the article.

6. The X-ray inspection apparatus according to claim 1, wherein
   the X-ray inspection apparatus furthermore includes a changing unit to change the setting value when the assessment unit has determined that the setting value is not suitable for inspection of the article.

7. The X-ray inspection apparatus according to claim 6, wherein:
   the inspection unit inspects the article on the basis of a plurality of inspection criteria;
   the setting unit is capable of setting a setting value for each of the inspection criteria; and the assessment unit determines, for each of the inspection criteria, whether or not the setting value set by the setting unit is suitable for inspection of the article.

8. The X-ray inspection apparatus according to claim 6, wherein
the inspection unit is configured to detect foreign substances included in the article.

9. The X-ray inspection apparatus according to claim 1, wherein:
the inspection unit inspects the article on the basis of a plurality of inspection criteria;
the setting unit is capable of setting a setting value for each of the inspection criteria; and
the assessment unit determines, for each of the inspection criteria, whether or not the setting value set by the setting unit is suitable for inspection of the article.

10. The X-ray inspection apparatus according to claim 9, wherein
the inspection unit is configured to detect foreign substances included in the article.

11. The X-ray inspection apparatus according to claim 1, wherein
the inspection unit is configured to detect foreign substances included in the article.

* * * * *